United States Patent [19]

Isowa et al.

[11] 3,972,773

[45] Aug. 3, 1976

[54] PROCESS FOR PRODUCING PEPTIDE

[75] Inventors: Yoshikazu Isowa, Tokyo; Takeshi Nagasawa, Koriyama; Katsumasa Kuroiwa, Koriyama; Koichi Narita, Koriyama, all of Japan

[73] Assignees: Sagami Chemical Research Center, Tokyo; Nitto Boseki Co., Ltd., both of Japan

[22] Filed: Apr. 29, 1975

[21] Appl. No.: 572,630

[52] U.S. Cl. .................................. 195/29; 195/30
[51] Int. Cl.$^2$ ...................................... C12D 13/06
[58] Field of Search ..................... 195/29.4, 30, 2; 260/112.5

[56] References Cited
UNITED STATES PATENTS 3,544,426    12/1970    Snellman ............................ 195/29

OTHER PUBLICATIONS

Neurath "The Proteins – Synthesis & Function of Peptides of Biological Interest" Academic Press 2nd edition, 1963, pp. 53–105.

*Primary Examiner*—A. Louis Monacell
*Assistant Examiner*—R. B. Penland
*Attorney, Agent, or Firm*—Oblon, Fisher, Spivak, McClelland & Maier

[57] ABSTRACT

A peptide having the formula:

X-A-B-C-Y wherein
A represents Ala., Gln., Asn., ω-BOC-Lys., Leu., Gly., Glu., $$\text{Glu, Pro;} \atop \text{OMe}$$

or
A represents $A_1 - A_2$ wherein $A_1$ represents a hydrophilic amino acid residue and $A_2$ represents Val., Met., Leu. or Gln.;
B represents Phe., Tyr., Leu., Met., Glu., Asp., Gln., Asn or Trp.;
C represents Phe., Leu., Ileu., Try., Cys-SBzl., Ser-OBzl., Trp. or Met.;
X represents an α-amino acid protective group; an amino acid residue having an N-terminal protective group or a peptide residue having an N-terminal protective group; Y represents a carboxyl protective group, an amino acid residue having a C-terminal protective group or a peptide residue having a C-terminal group, is produced in a process which comprises reacting a peptide having the formula

X-A-B-OH with an amino acid or a peptide having the formula

H-C-Y in the presence of enzyme pepsin.

9 Claims, No Drawings

PROCESS FOR PRODUCING PEPTIDE

BACKGROUND OF THE INVENTION

1. Field of the Invention

The present invention relates to a process for producing a peptide in the presence of pepsin.

2. Description of Prior Art

Recently, various peptides having physiological activity have been disclosed, and development of techniques for synthesis of peptides has been ongoing. Typical processes for producing peptides include an azide method; a mixed acid anhydride method; a dicyclohexyl carbodiimide method; and an active ester method. However, in accordance with these conventional processes, various disadvantages occur, e.g., racemization, side reactions, necessarily complicated temperature control, long reaction times, etc. Especially in the fragment condensation method, unavoidable racemization is a particularly bothersome disadvantage. In actuality, in any synthesis of peptides, the racemization problem is serious. When racemization occurs, the purity of the product is decreased and the separation of the impure isomer is necessitated. This is a severe disadvantage in an industrial operation.

In addition to the organic chemical processes, certain peptide synthes using the enzyme papain have been disclosed. (See, for example, O. K. Behrens and M. Bergmann; J. Biol. Chem., 129,587 (1939) and H. B. Milne and Warren Kilday; J. Org. Chem., 30, 64 (1965). Thereby, the racemization problem has been solved. However, these methods are applicable only to preparations of di- or tri-peptides. When a tetra- or higher peptide is synthesized by using a papain having varying substrate specificity, several side reactions involving hydrolysis of a peptide occur, e.g., transpeptidation and formation of plastein. Consequently, this scheme cannot be used for industrial peptide synthesis.

It is known that proteolytic enzymes (protease) have the characteristic property of hydrolyzing peptides in good reproducible operation, and under mild conditions without bothersome side reactions. Accordingly, the proteolytic enzymes have been utilized for various studies of chemical structures of polypeptides and proteins. By using them, the preliminary structures of various natural polypeptides such as insulin have been determined. One typical such enzyme is pepsin, classified among the digestive enzymes of endopeptitases (enzymes which are active to an inner bond of peptide chains) as a proteolytic enzyme.

It would be most desirable to have a process for production of a peptide which is free from the above disadvantages.

SUMMARY OF THE INVENTION

Accordingly, it is one object of this invention to provide a process for synthesis of a desired peptide by a simple operation in high yield.

It is another object of this invention to provide a process for synthesis of polypeptides, especially higher than tripeptides, by using the enzyme pepsin which is free from the defects of the known processes.

Briefly, these and other objects of the invention, as will hereinafter be made clear, have been attained by providing a process for producing a peptide having the formula:

X-A-B-C-Y  (III)

wherein

A represents alanine (Als), glutamine (Gln), asparagine (Asn), ω-BOC-lysine (Lys), leucine (Leu), glycine (Gly), glutamic acid (Glu),

or proline (Pro); or

A can be $A_1$—$A_2$, where $A_1$ represents a hydrophilic amino acid residue which can be Ala., Gln., Asn., ω-BOC-Lys., Leu., Gly., Glu,

or Pro., and $A_2$ represents valine (Val.), methionine (Met.), Leu. or Gln.;

B represents phenylalanine (Phe.), tyrosine (Tyr.), Leu., Met., Glu., aspartic acid (Asp.), Gln., Asn., or tryptophan (Trp.);

C represents Phe., Leu., isoleucin (Ileu.), Tyr., cysteine (Cys)-SBzl., serine (Ser)-OBzl., Trp., or Met.;

X represents an α-amino acid protective group, an amino acid residue having an N-terminal protective group or a peptide residue having an N-terminal protective group; and Y represents a carboxyl protective group, an amino acid residue having a C-terminal protective group or a peptide residue having a C-terminal protective group, (see ensuing discussion for explanation of terms used herein), which comprises reacting a peptide having the formula:

  (I)

with an amino acid or a peptide having the formula:

  (II)

in the presence of the enzyme pepsin.

DESCRIPTION OF THE PREFERRED EMBODIMENTS

The term "peptide" is given the definition as contained in The Organic Chemistry of Peptides, (Willy Interscience, 1970, Harry D. Law, page 6), while the meaning of the term "pepsin", especially pepsin titer, is illustrated in J. Gen. Physiol., M. Anson, Vol. 22, 79, (1938). The process of this invention is especially applicable for the sequential and the fragment condensation methods of producing peptides. When the process of this invention is applied to the fragment condensation method, which is remarkably advantageous when compared to the sequential method, the advantages of the process are quite significant.

In the process of the invention, the peptide having the formula (I) (hereinafter referred to as the C-component) is used as a starting material. Generally, it is preferred to use as a starting material peptides (including polypeptides and oligopeptides) having at least slight solubility in the medium, since insoluble peptides are inactive. The C-component should have a partial structure of condensation such that two or three specific amino acids in a specific order of bonding, i.e., the bond -A-B- in the formula (I) is in the reactive position. As long as this specific partial structure is included, various peptides can be used. The terminal group of the C-component, i.e., the α-position of the amino group, should be protected by an amino-protecting group such as a carbobenzoxy group (Z); a substituted carbobenzoxy group, e.g., p-methoxy benzyloxycarbonyl group (pMZ); a t-butyloxycarbonyl group (BOC) or a tosyl group (TOS), etc.

The amino acid or peptide having the formula (II) (hereinafter referred to as the N-component) which is the other starting material, should have at the reactive position specific amino acids such as phenylalanine, leucine, isoleucine, tyrosine, S-benzylcysteine, O-benzyl serine, tryptophan, or methionine. The terminal carboxyl group of the N-component should be protected by a carboxyl protecting group such as a methyl ester, an ethyl ester, a benzyl ester, a t-butyl ester or p-nitrobenzyl ester group; an amide group, a substituted amide group, e.g., a 2,4,6-trimethyl benzylamide group (TMB), a hydrazide or a derivative thereof. The N-component can be free or in the form of a salt, such as a hydrochloride, hydrobromide, trifluoroacetate, p-toluenesulfonate, or some other inorganic or organic salt.

Any object peptide unit with an N-component and a C-component selected from the above-mentioned scope, may be prepared by the process of this invention. The desired peptides can be produced by the fragment condensation method. In the process of the invention, the C-component and the N-component can be used in equivalent amounts. However, it is also possible to react them using an excess of one of them. The molar ratio of the N-component to the C-component is usually 1:5 ~ 5:1, preferably 1:2 ~ 2:1. In the reaction, it is preferable to use the N-component by dissolving it in an alkaline medium containing an alkali such as an alkali metal hydroxide or an alkaline earth metal hydroxide. It is necessary to carry out the reaction in a buffer solution having a pH of 2 – 6, at a temperature of 20° – 50°C. Suitable buffer solutions include citric acid buffer solution, Michaelis buffer solution, McIlvaine buffer solution, and other buffer solutions having a pH of 2 – 6. Buffer solutions having a pH of lower than 2 or higher than 6 should not be used because the yield is low. The preferred pH is 3 – 5, and the optimum pH is 4. When the temperature is lower than 20°C, a long time is required for completing the reaction. When the temperature is higher than 50°C, the activity of pepsin is remarkably decreased, and the yield is low. The preferred temperature is 30° – 40°C.

The pepsin used in the invention is a digestive endopeptitase enzyme. Pepsin having a pepsin titer of 1:5,000; 1:10,000; and 1:60,000 can be easily obtained. A crude pepsin can be used as long as it has high activity. A catalytic amount of pepsin is employed, preferably 0.4 – 400 mg of pepsin per 1 mmole of the starting materials.

The reaction is smoothly performed in a water medium or a water miscible medium such as methanol, ethanol, dioxane, dimethylformamide, or the like. The product is sparingly soluble in either water or the water miscible medium. Accordingly, it is precipitated as crystals from the reaction system. The crystals precipitated are filtered and are washed with an appropriate weak alkali aqueous solution, a weak acidic aqueous solution and water to obtain the pure product. The terminal protective group of the N-component and the terminal protective group of the C-component of the product can be subsequently removed in the conventional manner if desired.

Having generally described the invention, a more complete understanding can be obtained by reference to certain specific examples, which are included for purposes of illustration only and are not intended to be limiting unless otherwise specified.

EXAMPLE 1

A solution of 0.753 g (1.5 mmol) of HCl.H-Phe-Gly-Leu-Met-NH$_2$ (MW 502.1) in 40 ml of citric acid buffer solution (pH = 4.0) was added to a solution of 1.26 g (2.5 mmol) of α, ω-Boc-Lys-Phe-OH (MW 505.6) in 5 ml of 1N-NaOH and 30 ml of water was further added with stirring. Then, 0.2 g of pepsin (1:5000 manufactured by Mikuni Kagaku Sangyo K. K.) was added to the mixture with stirring at 40°C for 24 hours to react them. The resulting white precipitate was filtered by a glass filter (G-3) and was sequentially washed with 5% ammonia water, 5% citric acid aqueous solution and water. The product was dried above P$_2$O$_5$ under reduced pressure at 50°C to obtain 1.25 g of α, ω-Boc-Lys-Phe-Phe-Gly-Leu-Met-NH$_2$ having a melting point of 207° – 216°C (decomposition) and $[\alpha]_D^{25} = -38.8$ ($c$ = 0.5 DMF). The yield was 88.2%.

Elementary analysis (C$_{47}$H$_{72}$O$_{10}$N$_8$S = 941.210):

|  | C | H | N | S |
|---|---|---|---|---|
| Calculated (%) | 59.98 | 7.71 | 11.91 | 3.41 |
| Measured (%) | 59.74 | 7.71 | 11.74 | 3.42 |

REFERENCE EXAMPLE

A 4.0 g sample of α, ω-Boc-Lys-Phe-Phe-Gly-Leu-Met-NH$_2$ was dissolved in 100 ml of glacial acetic acid, and HCl gas was injected into the solution with stirring for 40 minutes to remove the protective Boc-group. After the reaction, the mixture was added to 500 ml of cooled ether to form a precipitate. The precipitate was filtered and dried above NaOH under reduced pressure to obtain 2.70 g of 2HCl.H-Lys-Phe-Phe-Gly-Leu-Met-NH$_2$ having a melting point of 168°–170°C (decomposition) and $[\alpha]_D^{25} = -16.0$ (c = 0.5 50% MeOH).

The yield was 78.0%.

Elementary analysis (C$_{37}$H$_{56}$O$_6$N$_8$S.2HCl.1(1/2) H$_2$O = 841.915):

|  | C | H | N | S | Cl |
|---|---|---|---|---|---|
| Calculated (%) | 52.97 | 7.04 | 13.31 | 3.52 | 8.66 |
| Measured (%) | 52.84 | 7.33 | 13.33 | 3.81 | 8.42 |

EXAMPLE 2

A solution of 0.753 g (1.5 mmol) of HCl.H-Phe-Gly-Leu-Met-NH$_2$ (MW 502.1) in 40 ml of citric acid buffer solution (pH = 4.0) was added to a solution of 1.0 g (2.5 mmol) of pMZ-Ala-Phe-OH (MW 400.4) in 5 ml of 1N NaOH, and 30 ml of water was further added with stirring. Then, 0.2 g of pepsin (1:5000 manufactured by Mikuni Kagaku Sangyo K. K.) was added to the mixture with stirring in an incubator at 40°C for 24 hours to react them. The resulting white precipitate was filtered, and was sequentially washed with 5% aq. NH$_4$OH, 5% citric acid aqueous solution and water. The product was dried above P$_2$O$_5$ under reduced pressure at 50°C to obtain 1.14 g of pMZ-Ala-Phe-Phe-Gly- Leu-Met-NH$_2$ having a melting point of 229° – 233°C and $[\alpha]_D^{25} = -55.0$ (c = 0.5 DMF).

The yield was 89.2%.

Elementary analysis (C$_{43}$H$_{57}$O$_9$S = 847.031):

|  | C | H | N | S |
|---|---|---|---|---|
| Calculated (%) | 60.81 | 6.92 | 11.43 | 3.92 |
| Measured (%) | 60.90 | 6.77 | 11.56 | 3.78 |

EXAMPLE 3

A 1.14 g sample (2.5 mmol) of pMZ-Gln-Phe-OH (MW 457.5) and a 0.75 g (1.5 mmol) of HCl.H-Phe-Gly-Leu-Met-NH$_2$ (MW 502.1) were used in accordance with the process of Example 1. The reaction was carried out at 40°C for 24 hours to obtain 1.05 g of pMZ-Gln-Phe-Phe-Gly-Leu-Met-NH$_2$ having a melting point of 236°–237°C, and $[\alpha]_D^{25} = -22.8$ (c = 1, DMSO). The yield was 77.5%.

Elementary analysis (C$_{45}$H$_{60}$O$_{10}$N$_8$S = 905.092):

(1.5 mmol) of HCl.H-Ileu-Gly-Leu-Met-NHDmB (MW 618.2) to obtain 1.30 g of pMZ-Ala-Phe-Ileu-Gly-Leu-Met-NHDmB having a melting point of 225°–227°C and $[\alpha]_D^{25} = -25.4$ (c = 1, DMF) wherein DmB represents 2,4-dimethoxybenzyl. In this example, 0.4 g of pepsin was used.

The yield was 82.2%.

Elementary analysis (C$_{49}$H$_{69}$N$_7$O$_{11}$S = 964.192):

|  | C | H | N | S |
|---|---|---|---|---|
| Calculated (%) | 61.04 | 7.21 | 10.17 | 3.33 |
| Measured (%) | 61.17 | 7.35 | 10.09 | 3.33 |

EXAMPLES 5 – 7

In accordance with the process of Example 1, except for reacting the C-components (2.5 mmol) and the N-components (2.5 mmol) as indicated in Table 1, the corresponding peptides were obtained. The results are shown in Table 1.

Table 1

| Example | C-component | N-component | Product | Yield (%) | Melting point (°C) | Optical rotation $[\alpha]_D^{25}$ | Elementary analysis (%) | | | |
|---|---|---|---|---|---|---|---|---|---|---|
|  |  |  |  |  |  |  | C | H | N | S |
| 5 | α,Ω-Boc-Lys-Phe-OH | H-Ileu-Gly-Leu-Met-NH$_2$ | α,ω-Boc-Lys-Phe-Ileu-Gly-Leu-Met-NH$_2$ | 94.4 | 242~246 | −25.6° (c=0.5 DMF) | C$_{44}$H$_{74}$N$_8$O$_{10}$S Calculated: 58.26 Found: 58.29 | 8.22 8.37 | 12.25 12.24 | 3.53 3.41 |
| 6 | Boc-Ala-Phe-OH | " | Boc-Ala-Phe-Ileu-Gly-Leu-Met-NH$_2$ | 63.3 | 231~238 | −26.6° (c=0.5 DMF) | C$_{36}$H$_{59}$N$_7$O$_8$S.½H$_2$O Calculated: 57.20 Found: 57.16 | 7.96 8.05 | 12.97 12.80 | 4.23 4.12 |
| 7 | pMZ-Leu-Met-OH | " | pMZ-Leu-Met-Ileu-Gly-Leu-Met-NH$_2$ | 96.9 | 247~250 | −39.2° (c=0.5 DMF) | C$_{39}$H$_{65}$N$_7$O$_9$S$_3$ Calculated: 55.76 Found: 55.58 | 7.80 7.83 | 11.67 11.57 | 7.63 7.84 |
| 8 | Boc-Gly-Ala-Phe-OH | H-Ileu-Gly-Leu-Met-NH$_2$ | Boc-Gly-Ala-Phe-Ileu-Gly-Leu-Met-NH$_2$ | 83.7 | 260~265 | −30.0° (c=0.5 DMF) | C$_{38}$H$_{62}$O$_9$N$_8$S Calculated: 56.56 Found: 56.46 | 7.74 7.78 | 13.88 13.57 | 3.97 4.12 |
| 9 | Boc-Gln-Gln-Phe-OH | H-Phe-Gly-Leu-Met-NH$_2$ | Boc-Gln-Gln-Phe-Phe-Gly-Leu-Met-NH$_2$ | 62.0 | 249~252 | −19.6° (c=1 DMSO) | C$_{46}$H$_{68}$H$_{10}$O$_{11}$S.H$_2$O Calculated: 55.97 Found: 55.90 | 7.15 7.10 | 14.19 14.21 | 3.52 3.48 |
| 10 | Boc-Ala-Phe-OH | H-Phe-Gly-Leu-Met-NH$_2$ | Boc-Ala-Phe-Phe-Gly-Leu-Met-NH$_2$ | 47.9 | 240~245 | −53.4° (c=0.5 DMF) | C$_{39}$H$_{57}$O$_8$N$_7$S Calculated: 59.75 Found: 59.49 | 7.33 7.33 | 12.50 12.24 | 4.09 4.18 |
| 11 | Boc-Pro-Ala-Phe-OH | H-Ileu-Gly-Leu-Met-NH$_2$ | Boc-Pro-Ala-Phe-Ileu-Gly-Leu-Met-NH$_2$ | 81.2 | 243~247 | −45.3° (c=0.5 DMSO) | C$_{41}$H$_{66}$N$_8$O$_9$S.H$_2$O Calculated: 56.92 Found: 56.80 | 7.92 7.68 | 12.95 13.00 | 3.71 3.46 |

|  | C | H | N | S |
|---|---|---|---|---|
| Calculated (%) | 59.71 | 6.68 | 12.38 | 3.54 |
| Measured (%) | 59.89 | 6.58 | 12.31 | 3.46 |

EXAMPLE 4

In accordance with the process of Example 1, the reaction was carried out by using 1 g sample (2.5 mmol) of pMZ-Ala-Phe-OH (MW 400.4) and 0.93 g

EXAMPLE 12

A solution of 0.539 g (2.5 mmol) of HCl.H-Phe-OCH$_3$ (MW=215.67) in 40 ml of citric acid buffer solution (pH = 4.0) was added to a solution of 1.00 g (2.5 mmol) of pMZ-Ala-Phe-OH (MW=400.42) in 5 ml of 1N-NaOH, and 20 ml of water was further added with stirring. A 0.2 g sample of pepsin (1:5000) was added to the mixture with stirring at 40°C for 24 hours to react them. The resulting white precipitate was filtered by a glass filter (G-3), and was washed sequentially with 5% ammonia water, and water. The product was dried under reduced pressure and recrystallized from methanol to obtain pMZ-Ala-Phe-Phe-OCH₃ having a melting point of 189°–192°C, and $[\alpha]_D^{20} = -17.2$ (c = 1, DMF).

The yield was 59.3%.

Elementary analysis ($C_{31}H_{35}N_3O_7$ = 561.641):

|  | C | H | N |
|---|---|---|---|
| Calculated (%) | 66.30 | 6.28 | 7.48 |
| Measured (%) | 66.23 | 6.23 | 7.53 |

EXAMPLES 13–21

In accordance with the process of Example 12, except for reacting the C-components (2.5 mmol) and the N-components (2.5 mmol) according to Table 2, the corresponding peptides were obtained. The results are shown in Table 2.

EXAMPLE 25

The process of Example 12 was repeated except using 30 ml of water and reacting for 10 hours to obtain the same object product. The yield was 50.0%.

EXAMPLE 26

A solution of 2.5 mmol of HCl.H-Leu-Met-NH₂ in 40 ml of citric acid buffer solution (pH = 4.0) was added to a solution of 2.5 mmol of pMZ-Ala-Phe-OH in 5 ml of 1N-NaOH, and then 0.2 g of the pepsin of Example 8 was added at 40°C for 24 hours to react them. The resulting white precipitate was washed and dried in accordance with the process of Example 8. It was recrystallized from MeOH-H₂O to obtain 1.02 g of pMZ-Ala-Phe-Leu-Met-NH₂ having a melting point of 218°–219°C and $[\alpha]_D^{20} = 31.6$ (c = 0.5 DMF). The yield was 63.3%.

Elementary analysis ($C_{32}H_{45}N_5O_7S$ = 643.809):

Table 2

| Example | C-component | N-component | Product | Yield (%) | m.p. (°C) | $[\alpha]_D^{20}$ | Elementary analysis C H N S | Recrystallizaton |
|---|---|---|---|---|---|---|---|---|
| 13 | pMZ-Ala-Phe-OH | HCl.H-Try-OCH₃ | pMZ-Ala-Phe-Tyr-OCH₃ | 45.6 | 179~183 | +3.7° (c=0.5 DMF) | C 63.80 6.16 7.70<br>F 63.87 6.13 7.19 | DMF-MeOH-H₂O |
| 14 | " | HCl.H-Cys-OCH₃<br>S-Bzl | pMZ-Ala-Phe-Cys-OCH₃<br>S-Bzl | 48.4 | 164~166 | −27.8° ( " ) | C 63.24 6.14 6.91 5.28<br>F 63.09 5.98 6.97 5.15 | MeOH |
| 15 | " | HCl.H-Ileu-OCH₃ | pMZ-Ala-Phe-Ileu-OCH₃ | 7.0 | 170~175 | −14.2° (c=1 DMF) | C 64.15 6.98 8.08<br>F 63.99 7.00 8.22 | ethyl-acetate-petroleum ether |
| 16 | " | HCl.H-Ser-OCH₃<br>OCH₂φ | pMZ-Ala-Phe-Ser-OCH₃<br>OCH₂φ | 18.8 | 158~163 | −23.0° (c=1 MeOH) | C 64.96 6.30 7.10<br>F 65.09 6.45 7.41 | AcOEt-petroleum ether |
| 17 | " | Tos.OH-H-Phe-OCH₂φ | pMZ-Ala-Phe-Phe-OCH₂φ | 90.4 | 158~163 | −14.6° (c=1 DMF) | C 69.69 6.16 6.59<br>F 69.76 5.99 6.49 | DMF-ether-petroleum ether |
| 18 | " | HBr.H-Phe-NH₂ | pMZ-Ala-Phe-Phe-NH₂ | 55.6 | 241~242 | −36.1° ( " ) | C 65.92 6.27 10.25<br>F 65.64 6.23 10.14 | DMF-MeO-Et₂O |
| 19 | " | TFA.H-Phe-NHOCH₂φ | pMZ-Ala-Phe-Phe-NHOCH₂φ | 13.9 | 242~244 | −14.8° (c=0.5 DMF) | C 68.08 6.18 8.58<br>F 68.00 6.29 8.79 | DMF-MeOH-H₂O |
| 20 | " | 2HBr.H-Phe-NHNH₂ | pMZ-Ala-Phe-Phe-NHNH₂ | 52.9 | 228~230 | −21.8° (c=1 DMF) | C 64.16 6.28 12.47<br>F 63.93 6.29 12.29 | DMF-MeOH-Et₂O |
| 21 | " | HCl.H-Phe-Gly-NH₂ | pMZ-Ala-Phe-Phe-Gly-NH₂ | 51.4 | 232~233 | −34.1° ( " ) | C 63.69 6.18 11.60<br>F 63.43 6.14 11.43 | DMF-MeOH-ether |

Note:
Bzl : benzyl group,
φ: phenyl group.
C : Calculated
D : Found

EXAMPLE 22

The process of Example 12 was repeated except using 30 ml of water and 0.1 g of pepsin (1:10000), and reacting for 18 hours to obtain pMZ-Ala-Phe-Phe-OCH₃ having a melting point of 189°–193°C. The yield was 51.3%.

EXAMPLE 23

The process of Example 12 was repeated except using 30 ml of water and reacting for 18 hours to obtain pMZ-Ala-Phe-Phe-OCH₃ having a melting point of 187°–192°C. The yield was 59%.

EXAMPLE 24

The process of Example 22 was repeated except using 0.2 g of pepsin (1:1000) to obtain pMZ-Ala-Phe-Phe-OCH₃ having a melting point of 188°–193°C. The yield was 65.8%.

|  | C | H | N | S |
|---|---|---|---|---|
| Calculated (%) | 59.70 | 7.05 | 10.88 | 4.98 |
| Measured (%) | 59.94 | 7.19 | 10.78 | 4.92 |

EXAMPLE 27

A solution of 0.995 g (2.5 mmol) of 2HBr.H-Phe-Gly-NHNH₂ (MW = 398.105) in 40 ml of citric acid buffer solution of Example 12 was added to a solution of 1.50 g (3.75 mmol) of pMZ-Ala-Phe-OH in 7.5 ml of 1N-NaOH, and 30 ml of water was further added with stirring. The reaction was carried out in accordance with the process of Example 12. The resulting precipitate was washed and dried and recrystallized from DMF-MeOH-Et₂O to obtain 0.945 g of pMZ-Ala-Phe-Phe-Gly-NHNH₂ having a melting point of 208°–210°C, and $[\alpha]_D^{23} = -31.8$ (c=1 DMF). The yield was 61.2%.

Elementary analysis ($C_{32}H_{38}N_6O_7$ . 1/3 H₂O=624.701):

|              | C     | H    | N     |
|--------------|-------|------|-------|
| Calculated (%) | 61.52 | 6.23 | 13.45 |
| Measured (%)   | 61.38 | 6.25 | 13.38 |

EXAMPLE 28

A solution of 2.5 mmol of HCl.H-Phe-OCH$_3$ in 40 ml of citric acid buffer solution of Example 8 was added to a solution of 1.47 g (40 mmol) of pMZ-Ala-Leu-OH(MW=366.4) in 5 ml of 1N-NaOH, and then the reaction was carried out in accordance with the process of Example 26. The resulting precipitate was washed and dried to obtain 0.302 g of pMZ-Ala-Leu-Phe-OCH$_3$ having a melting point of 187°–191°C, and $[\alpha]_D^{23} = -18.0$ (c=0.5 DMF). The yield was 22.9%.

Elementary analysis (C$_{28}$H$_{37}$N$_3$O$_7$ . 1/3 H$_2$O = 533.628):

|              | C     | H    | N    |
|--------------|-------|------|------|
| Calculated (%) | 63.02 | 7.11 | 7.87 |
| Measured (%)   | 62.90 | 6.97 | 7.97 |

EXAMPLE 29

A solution of 0.793 g (2.5 mmol) of HBr.H-Phe-Gly-OCH$_3$ (MW=317.18) in the citric acid buffer solution of Example 8 was added to a solution of 1.50 g (3.75 mmol) of pMZ-Ala-Phe-OH in 5 ml of 1N-NaOH and then 20 ml of water was further added. The reaction was carried out in accordance with the process of Example 8. The resulting precipitate was washed, dried and recrystallized to obtain 1.46 g of pMZ-Ala-Phe-Phe-Gly-OCH$_3$ having a melting point of 227°–229°C and $[\alpha]_D^{23} = -26.7$ (c=1 DMF). The yield was 94.9%.

Elementary analysis (C$_{33}$H$_{35}$N$_4$O$_8$ = 618.693):

|              | C     | H    | N    |
|--------------|-------|------|------|
| Calculated (%) | 64.07 | 6.19 | 9.06 |
| Measured (%)   | 63.79 | 6.32 | 8.96 |

EXAMPLE 30

In accordance with the process of Example 28, the reaction was carried out by using 4.0 mmol of pMZ-Ala-Met-OH and 2.5 mmol of HCl.H-Phe-OCH$_3$ to obtain 0.3413 g of pMZ-Ala-Met-Phe-OCH$_3$ having a melting point of 153°–167°C and $[\alpha]_D^{23} = 17.4$ (c = 0.5 DMF). The yield was 24.6%.

Elementary analysis (C$_{27}$H$_{35}$N$_3$O$_7$S = 545.660):

|              | C     | H    | N    | S    |
|--------------|-------|------|------|------|
| Calculated (%) | 59.43 | 6.47 | 7.70 | 5.88 |
| Measured (%)   | 59.82 | 6.38 | 7.78 | 5.54 |

EXAMPLE 31

The reaction of Example 28 was repeated except using HCl.H-Phe-Gly-OEt (2.5 mmol) instead of HCl.H-Phe-OCH$_3$ (2.5 mmol). The product was washed with 5% ammonia water, and then with water. It was dried above P$_2$O$_5$ to obtain 0.8153 g of pMZ-Ala-Leu-Phe-Gly-OEt having a melting point of 175°–192°C and $[\alpha]_D^{23} = -23.4$ (c = 0.5 DMG). The yield was 54.5%.

Elementary analysis (C$_{31}$H$_{42}$N$_4$O$_8$ = 598.703):

|              | C     | H    | N    |
|--------------|-------|------|------|
| Calculated (%) | 62.19 | 7.07 | 9.36 |
| Measured (%)   | 62.06 | 7.01 | 9.20 |

EXAMPLE 32

A solution of 1.5 mmol of HCl.H-Ileu-Gly-Leu-Met-NH$_2$ (MW = 468.1) in 40 ml of the citric acid buffer solution of Example 12 was added to a solution of 2.5 mmol of pMZ-Ala-Phe-OH in 5 ml of 1N-NaOH and then was reacted for 48 hours at 40°C in the presence of 0.2 g of the pepsin of Example 12. The resulting precipitate was dried above P$_2$O$_5$ at 60°C for 18 hours to obtain 1.10 g of pMZ-Ala-Phe-Ileu-Gly-Leu-Met-NH$_2$ having a melting point of 253.5°–255°C and $[\alpha]_D^{23} = -42.4$ (c = 1, AcOH).

The yield was 90%.

EXAMPLE 33

A solution of 0.702 g (1.5 mmol) of HCl.H-Ileu-Gly-Leu-Met-NH$_2$ (MW = 468.1) in 40 ml of citric acid buffer solution of Example 12 was added to a solution of 1.15 g (2.5 mmol) of BOC-Asn-Ala-Phe-OH (MW = 450.5) in 5 ml of 1 N-NaOH in the same manner as in Example 22. The precipitate was sequentially washed with 5% ammonia water, 5% citric acid aqueous solution and water. The product was dried above P$_2$O$_5$ to obtain 1.052 g of BOC-Asn-Ala-Phe-Ileu-Gly-Leu-Met-NH$_2$ having a melting point of 256°–260°C and $[\alpha]_D^{23} = -36.2$ (c = 0.5 DMF). The yield was 81.0%.

Elementary analysis (C$_{40}$H$_{65}$N$_9$O$_{11}$S = 864.082):

|              | C     | H    | N     | S    |
|--------------|-------|------|-------|------|
| Calculated (%) | 55.60 | 7.58 | 14.59 | 3.71 |
| Measured (%)   | 55.43 | 7.69 | 14.31 | 3.65 |

EXAMPLE 34

The process of Example 28 was repeated except using 1.31 g (2.5 mmol) of pMZ-Gln-Ala-Phe-OH (MW = 528.5), and 0.702 g (1.5 mmol) of 2HCl.H-Ileu-Gly-Leu-Met-NH$_2$ (MW = 468.1) instead of pMZ-Ala-Leu-OH and HCl.H-Phe-OCH$_3$ to obtain 1.04 g of pMZ-Gln-Ala-Phe-Ileu-Gly-Leu-Met-NH$_2$ having a melting point of 258°–260°C (decomposition). The yield was 74.5%.

Elementary analysis (C$_{74}$H$_{67}$N$_7$O$_{11}$S = 930.142):

|              | C     | H    | N     | S    |
|--------------|-------|------|-------|------|
| Calculated (%) | 56.82 | 7.26 | 13.55 | 3.45 |
| Measured (%)   | 56.56 | 7.16 | 13.49 | 3.25 |

EXAMPLE 35

A 1.60 g sample (4 mmol) of pMZ-Ala-Phe-OH was dissolved in 1N-NaOH and 0.54 g (2.5 mmol) of HCl.H-Phe-OCH$_3$ was dissolved in each of several 40 ml samples of citric acid buffer solution each having a different pH value. The two solutions were mixed and 30 ml of water was added in each case. 0.2 g of pepsin of Example 12 was added to each mixture at 40°C for 24 hours to react them. The resulting precipitate was washed sequentially with 5% ammonia water, 5% citric acid aqueous solution, and water. The product was dried above P$_2$O$_5$ at 50°C to obtain pMZ-Ala-Phe-Phe-OCH$_3$. The pH's of the various citric acid buffer solutions and the corresponding yields are shown in Table 3.

TABLE 3

| pH | Yield (%) | m.p. (°C) | $[\alpha]_D^{25}$ (c = 1, DMF) |
|---|---|---|---|
| 2.38 | 61.1 | 170–173 | −18.4° |
| 3.28 | 74.6 | 185–189 | −16.7° |
| 4.08 | 99.9 | 186–189 | −18.0° |
| 5.02 | 64.0 | 189–190 | −17.2° |

EXAMPLE 36

A solution of 2 mmol of 2HBr.H-Phe-Gln-NHNH$_2$ in 40 ml of citric acid buffer solution (pH = 4.0) was added to a solution of 3.75 mmol of pMZ-Ala-Tyr-OH in 1N-NaOH. 0.2 g of pepsin was added to the mixture at 25°C for 48 hours to react them in accordance with the process of Example 8 to obtain pMZ-Ala-Tyr-Phe-Gln-NHNH$_2$ having a melting point of 245°–248°C (decomposition) and $[\alpha]_D^{22}$ = −4.6 (c=1, DMSO). The yield was 57.8%.

Elementary analysis (C$_{35}$H$_{45}$N$_7$O$_8$.H$_2$O = 725.806):

|  | C | H | N |
|---|---|---|---|
| Calculated (%) | 57.92 | 6.52 | 13.52 |
| Measured (%) | 57.98 | 6.35 | 13.54 |

EXAMPLE 37

The process of Example 12 was repeated except using 2.5 mmol of pMZ-Ala-Phe-Ala-Phe-OH and 2.5 mmol of HCl.H-Leu-Met-NH-DMB and reacting for 14 hours to obtain pMZ-Ala-Phe-Ala-Phe-Leu-Met-NH-DMB having a melting point of 250° – 260°C and $[\alpha]_D^{25}$ = −21.0 (c = 0.4 DMF). The yield was 70%.

EXAMPLE 38

The process of Example 12 was repeated except using 2.5 mmol of pMZ-Ala-Phe-Ala-Phe-OH and 2.5 mmol of HCl.H-Ileu-Gly-OEt and reacting for 9 hours to obtain pMZ-Ala-Phe-Ala-Phe-Ileu-Gly-OEt having a melting point of 248°–252°C. The yield was 63%.

EXAMPLE 39

A solution of 0.216 g (10 mmol) of HCl.H-Phe-OCH$_3$ (MW 215.5) in 40 ml of citric acid buffer solution (pH = 4.0) was added to a solution of 0.495 g (10 mmol) of Z-Pro-Val-Phe-OH (MW 495) in 10 ml of 1N-NaOH, and 30 ml of water was further added with stirring. A 0.1 g sample of pepsin (1:10000) was added to the mixture with stirring at 40°C for 24 hours to react them. The resulting white precipitate was filtered by a glass filter (G-3) and was sequentially washed with 5% ammonia water, 5% citric acid aqueous solution and water. The product was dried above P$_2$O$_5$ under reduced pressure at 50°C to obtain 0.244 g of Z-Pro-Val-Phe-Phe-OCH$_3$ having a melting point of 199°–201°C and $[\alpha]_D^{30}$ = −33.2 (c = 1, DMF). The yield was 37.2%.

EXAMPLE 40

A solution of 0.216 g (10 mmol) of HCl.H-Phe-OCH$_3$ (MW 215.5) in 40 ml of citric acid buffer solution (pH = 4.0) was added to a solution of 0.421 g of BOC-Gly-Val-Phe-OH (MW 421) in 10 ml of 1N-NaOH and 30 ml of water was further added with stirring. Then, 0.1 g of pepsin (1:10000) was added to the mixture with stirring in an incubator at 40°C for 24 hours to react them. 0.414 g of BOC-Gly-Val-Phe-Phe-OCH$_3$ having a melting point of 193° – 196°C and $[\alpha]_D^{30}$ = −14.8 (c = 1, DMF) was obtained. The yield was 71.2%.

EXAMPLE 41

The process of Example 39 was repeated except changing the molar ratio of Z-Pro-Val-Phe-OH : HCl.H-Phe-OCH$_3$ to 2:1 to obtain 0.297 g of the same product as in Example 39. The yield was 51%.

EXAMPLE 42

The process of Example 40 was repeated except using tartaric acid-tartaric buffer solution (pH = 4) instead of citric acid buffer solution to obtain 0.426 g of the same product as in Example 40. The yield was 73.3%.

EXAMPLE 43

The process of Example 40 was repeated except using disodium hydrogen phosphate-citric acid buffer solution (pH = 4) instead of the citric acid buffer solution to obtain 0.396 g of the same product as in Example 40. The yield was 68%.

EXAMPLE 44

The process of Example 39 was repeated except reacting for 20 hours with 0.2 g of pepsin (1:5000) to obtain 0.230 g of the same product as in Example 35. The yield was 35%.

EXAMPLES 45–65

In accordance with the process of Example 39, by reacting the C-components (10 mmol) and the N-components (10 mmol) shown in Table 4, the corresponding peptides were obtained. The results are shown in Table 4.

Table 4

| Example | C-component | N-component | Product | Yield (%) | m.p. (°C) | $[\alpha]_D^{30}$ |
|---|---|---|---|---|---|---|
| 45 | pMZ-Gly-Val-Phe-OH | HCl.H-Phe-OCH$_3$ | pMZ-Gly-Val-Phe-Phe-OCH$_3$ | 74.3 | 175 178 | −15.1° (c=1, DMF) |
| 46 | Z-Pro-Val-Phe-OH | HCl.H-Phe-Gly-OC$_2$H$_5$ | Z-Pro-Val-Phe-Phe-Gly-OC$_2$H$_5$ | 67.2 | 215 216 | −31.2° (c=0.5,DMF) |
| 47 | BOC-Pro-Val-Phe-OH | HCl.H-Phe-Gly-OC$_2$H$_5$ | BOC-Pro-Val-Phe-Phe-Gly-OC$_2$H$_5$ | 34.4 | 208 210 | −46.8° (c=0.5,DMF) |
| 48 | BOC-Gly-Val-Phe-OH | HCl.H-Phe-Gly-OC$_2$H$_5$ | BOC-Gly-Val-Phe-Phe-Gly-OC$_2$H$_5$ | 45.1 | 185 187 | −14.4° (c=0.5,DMF) |
| 49 | pMZ-Gly-Val-Phe-OH | HCl.H-Phe-Gly-OC$_2$H$_5$ | pMZ-Gly-Val-Phe-Phe-Gly-OC$_2$H$_5$ | 75.0 | 200 212 | −18.6° (c=0.5,DMF) |

Table 4-continued

| Example | C-component | N-component | Product | Yield (%) | m.p. (°C) | $[\alpha]_D^{30}$ |
|---|---|---|---|---|---|---|
| 50 | pMZ-Gly-Leu-Phe-OH | HCl.H-Phe-OCH$_3$ | pMZ-Gly-Leu-Phe-Phe-OCH$_3$ | 77.0 | 178–181 | −26.4° (c=1, DMF) |
| 51 | BOC-Pro-Leu-Phe-OH | HCl.H-Phe-Gly-OC$_2$H$_5$ | BOC-Pro-Leu-Phe-Phe-Gly-OC$_2$H$_5$ | 62.9 | 217–219 | −48.2° (c=1, DMF) |
| 52 | BOC-Gly-Leu-Phe-OH | HCl.H-Phe-Gly-OC$_2$H$_5$ | BOC-Gly-Leu-Phe-Phe-Gly-OC$_2$H$_5$ | 54.5 | 160–164 | −34.8° (c=0.5,DMF) |
| 53 | pMZ-Gly-Leu-Phe-OH | HCl.H-Phe-Gly-OC$_2$H$_5$ | pMZ-Gly-Leu-Phe-Phe-Gly-OC$_2$H$_5$ | 59.0 | 170–172 | −29.2° (c=0.5,DMF) |
| 54 | BOC-Pro-Met-Phe-OH | HCl.H-Phe-OCH$_3$ | BOC-Pro-Met-Phe-Phe-OCH$_3$ | 45.7 | 145–149 | −39.4° (c=0.5,DMF) |
| 55 | BOC-Gly-Met-Phe-OH | HCl.H-Phe-OCH$_3$ | BOC-Gly-Met-Phe-Phe-OCH$_3$ | 44.3 | 153–154 | −12.6° (c=0.5,DMG) |
| 56 | pMZ-Gly-Met-Phe-OH | HCl.H-Phe-OCH$_3$ | pMZ-Gly-Met-Phe-Phe-OCH$_3$ | 69.6 | 175–179 | −17.2° (c=1,DMF) |
| 57 | BOC-Pro-Met-Phe-OH | HCl.H-Phe-Gly-OC$_2$H$_5$ | BOC-Pro-Met-Phe-Phe-Gly-OC$_2$H$_5$ | 51.2 | 208–210 | −33.2° (c=0.5,DMF) |
| 58 | pMZ-Gly-Met-Phe-OH | HCl.H-Phe-Gly-OC$_2$H$_5$ | pMZ-Gly-Met-Phe-Phe-Gly-OC$_2$H$_5$ | 61.9 | 175–177 | −27.0° (c=1, DMF) |
| 59 | BOC-Ala-Met-Phe-OH | HCl.H-Phe-Gly-OC$_2$H$_5$ | BOC-Ala-Met-Phe-Phe-Gly-OC$_2$H$_5$ | 60.8 | 211–214.5 | −25.1° (c=1, DMF) |
| 60 | BOC-Asn-Met-Phe-OH | HCl.H-Phe-Gly-OC$_2$H$_5$ | BOC-Asn-Met-Phe-Phe-Gly-OC$_2$H$_5$ | 71.8 | 216–220 | −60.0° (c=1, DMF) |
| 61 | BOC-Gln-Met-Phe-OH | HCl.H-Phe-Gly-OC$_2$H$_5$ | BOC-Gln-Met-Phe-Phe-Gly-OC$_2$H$_5$ | 72.0 | 220–222 | −25.0° (c=1, DMF) |
| 62 | BOC-Ala-Leu-Tyr-OH | H-Leu-Val-OCH$_3$ | BOC-Ala-Leu-Tyr-Leu-Val-OCH$_3$ | 37.1 | 199–201 | −40.6° (c=1,DMF) |
| 63 | BOC-Ala-Leu-Tyr-OH | H-Leu-Val-Cys-Gly-NHNH$_2$ SPMBzl | BOC-Ala-Leu-Tyr-Leu-Val-Cys-Gly-NHNH$_2$ SPMBzl | 76.5 | >250 (dec.) | −50.1° (c=1, DMF) |
| 64 | BOC-Arg-Gly-Phe-OH \| NO$_2$ | H-Phe-Tyr-NHNH$_2$ \| OBzl | BOC-Arg-Gly-Phe-Phe- \| NO$_2$ Tyr-NHNH$_2$ \| OBzl | 87.3 | 205–207 | −19.6° (c=1, DMF) |
| 65 | BOC-Arg-Gly-Phe-OH \| NO$_2$ | H-Phe-Tyr-Thr-NHNH$_2$ \| OBzl | BOC-Arg-Gly-Phe-Phe- \| NO$_2$ Tyr-Thr-NHNH$_2$ \| OBzl | 85.2 | 219–220 | −16.0° (c=1, DMF) |

Note:
-SPMBzl represents -S-Para-methoxybenzyl.

EXAMPLE 66

A solution of 0.47 g (10 mmol) of HCl.H-Ileu-Gly-Leu-Met-NH$_2$ (MW 468.1) in 40 ml of citric acid buffer solution was added to a solution of 0.38 g (10 mmol) of

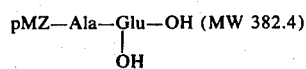

pMZ—Ala—Glu—OH (MW 382.4)
           |
           OH in 10 ml of 1N NaOH, and 30 ml of water was further added with stirring. 0.1 g of pepsin (1:10000) was added to the mixture with stirring at 40°C for 24 hours to react them. The resulting white precipitate was filtered by a glass filter (G-3) and was sequentially washed with 5% ammonia water, 5% citric acid aqueous solution and water. The product was dried above P$_2$O$_5$ under reduced pressure at 50°C to obtain 0.48 g of

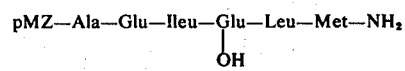

pMZ—Ala—Glu—Ileu—Glu—Leu—Met—NH$_2$
              |
              OH having a melting point of 214°–217°C and $[\alpha]_D^{30}$ = −23.8° (c = 0.5, DMF). The yield was 60.3%. The elementary analysis of the product corresponded to the theoretical value within experimental limits.

EXAMPLE 67

The process of Example 66 was repeated except changing the molar ratio of

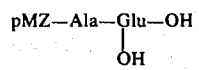

pMZ—Ala—Glu—OH
           |
           OH and HCl.H-Ileu-Gly-Leu-Met-NH₂ to 2:1 to obtain 0.68 g of the same product as in Example 66. The yield was 85.3%.

EXAMPLE 68

The process of Example 67 was repeated except using disodium hydrogen phosphate-citric acid buffer solution (pH =4) instead of citric acid buffer solution to obtain the same product as in Example 67. The yield was 84%.

EXAMPLES 69 –75

In accordance with the process of Example 66, by reacting the C-components (10 mmol) and the N-components (10 mmol) of Table 5, the corresponding peptides were obtained. The results are shown in Table 5.

Table 5

| Example | C-component | N-component | Product | Yield (%) | m.p. (°C) | $[\alpha]_D^{30}$ |
|---|---|---|---|---|---|---|
| 69 | pMZ-Glu-Phe-OH<br>\|<br>OCH₃ | HCl.H-Phe-OCH₃ | pMZ-Glu-Phe-Phe-OCH₃<br>\|<br>OCH₃ | 59.9 | 183–187 | −15.4° (c=1,DMF) |
| 70 | pMZ-Ala-Asn-OH | HCl.H-Ileu-Gly-Leu-Met-NH₂ | pMZ-Ala-Asn-Ileu-Gly-Leu-Met-NH₂ | 31.0 | 252–255 | −41.8° (c=1,DMSO) |
| 71 | pMZ-Ala-Trp-OH | HCl.H-Phe-Val-OCH₃ | pMZ-Ala-Trp-Phe-Val-OCH₃ | 60.0 | 210–216 | −32.0° (c=0.5,DMF) |
| 72 | pMZ-Ala-Trp-OH | HCl.H-Met-Gly-OCH₃ | pMZ-Ala-Trp-Met-Gly-OCH₃ | 21.7 | 163–167 | — |
| 73 | pMZ-Ala-Phe-OH | HCl.H-Trp-OCH₃ | pMZ-Ala-Phe-Trp-OCH₃ | 65.7 | 186–187 | −1.4° (c=0.5,DMF) |
| 74 | Z-Glu-Phe-OH | HCl.H-Ileu-Gly-Leu-Met-NH₂ | Z-Glu-Phe-Ileu-Gly-Leu-Met-NH₂ | 84 | 245–248 | −30.1° (c=1, DMF) |
| 75 | Z-Glu-Phe-OH | HCl.H-Phe-OCH₃ | Z-Glu-Phe-Phe-OCH₃ | 63 | 181–184 | −19.7° (c=1, DMF) |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for producing a peptide having the formula:

X-A-B-C-Y wherein

A represents Ala., Gln., Asn., ω-BOC-Lys., Leu., Gly., Glu.,

Glu, Pro;
OMe or

A represents A₁ — A₂, wherein A₁ represents a hydrophilic amino acid residue and A₂ represents Val., Met., Leu. or Gln.;

B represents Phe., Tyr., Leu., Met., Glu., Asp., Gln., Asn or Trp.;

C represents Phe., Leu., Ileu., Tyr., Cys-SBzl., Ser-OBzl., Trp. or Met.;

X represents an α-amino acid protective group, an amino acid residue having an N-terminal protective group or a peptide residue having an N-terminal protective group;

Y represents a carboxyl protective group, an amino acid residue having a C-terminal protective group or a peptide residue having a C-terminal protective group, which comprises reacting a peptide having the formula:

X-A-B-OH with an amino acid or peptide having the formula:

H-C-Y neither of which reactants need be activated, in the presence of enzyme pepsin employing a pH of from 2 to 6 and a temperature of 20° – 50°C.

2. The process of claim 1 which comprises using a peptide having the formula:

X-A-B-OH wherein A represents Ala., Gln., Asn., ω-BOC-Lys., Leu., or Gly.; B represents Phe., Tyr., Leu., or Met.; and X is defined as in claim 1.

3. The process of claim 1 which comprises using a peptide having the formula:

X-A-B-OH wherein A represents Glu.,

or Pro.; and B and X are defined as in claim 1.

4. The process of claim 1 which comprises using a peptide having the formula:

X-A₁ - A₂ - B - OH wherein A₁ represents a hydrophilic amino acid residue; A₂ represents Val., Met., Leu. or Gln.; and B and X are defined as in claim 1.

5. The process of claim 1 which comprises using an amino acid or a peptide having the formula:

H-C-Y wherein C represents Phe., Leu., Ileu., Tyr., Cys-SBzl., or Ser-OBzl; and Y is defined as in claim 1.

6. The process of claim 1 wherein the reaction is performed at 20° – 50°C in a buffer solution having a pH of 2 – 6.

7. The process of claim 1 wherein the molar ratio of the peptide having the formula:

X-A-B-OH to the amino acid or peptide having the formula:

H-C-Y is 1:5 to about 5:1.

8. The process of claim 1 wherein the amount of pepsin is 0.4 – 400 mg per 1 mmole of starting materials.

9. The process of claim 4 wherein $A_1$ is Ala., Gln., Asn., ω-BOC-Lys, Leu., Gly., Glu., $$\begin{matrix} \text{Glu} \\ | \\ \text{OMe} \end{matrix}$$

or Pro.

* * * * *